United States Patent [19]

Berthold

[11] Patent Number: 4,460,586
[45] Date of Patent: Jul. 17, 1984

[54] 2-CYANO-4-(2-HYDROXY-3-SUBSTITUTED-AMINOPROPOXY) INDOLES

[75] Inventor: Richard Berthold, Bottmingen, Switzerland

[73] Assignee: Sandoz Ltd., Basel, Switzerland

[21] Appl. No.: 338,592

[22] Filed: Jan. 11, 1982

[30] Foreign Application Priority Data

Jan. 16, 1981 [CH] Switzerland .......................... 275/81
Jan. 26, 1981 [CH] Switzerland .......................... 475/81
Feb. 9, 1981 [CH] Switzerland .......................... 846/81
Feb. 9, 1981 [CH] Switzerland .......................... 849/81
Feb. 9, 1981 [CH] Switzerland .......................... 852/81

[51] Int. Cl.³ .............. C07D 403/12; C07D 401/12; C07D 209/30; A61K 31/495; A61K 31/475
[52] U.S. Cl. .................................. 424/250; 544/373; 546/201; 424/262; 548/505
[58] Field of Search .................. 544/373; 546/201; 424/250, 262; 260/326.14 R

[56] References Cited

U.S. PATENT DOCUMENTS

| | | | |
|---|---|---|---|
| 3,699,123 | 10/1972 | Seemann et al. .......... | 546/201 |
| 3,929,793 | 12/1975 | Popelak et al. .......... | 544/373 |
| 4,061,641 | 12/1977 | Archibald et al. .......... | 546/201 |
| 4,140,691 | 2/1979 | Weston et al. .......... | 546/201 |
| 4,146,630 | 3/1979 | Kampe et al. .......... | 546/201 |
| 4,234,584 | 11/1980 | Lattrell et al. .......... | 544/373 |
| 4,264,599 | 4/1981 | Eichenberger et al. .......... | 546/201 |
| 4,288,442 | 9/1981 | Friebe et al. .......... | 546/201 |
| 4,304,915 | 12/1981 | Berthold .......... | 546/201 |
| 4,351,838 | 9/1982 | Hasspacher .......... | 546/205 |
| 4,361,562 | 11/1982 | Berthold .......... | 424/250 |

FOREIGN PATENT DOCUMENTS

| | | | |
|---|---|---|---|
| 5828 | 12/1979 | European Pat. Off. | |
| 2302717 | 1/1973 | Fed. Rep. of Germany | 546/201 |
| 1410783 | 10/1975 | United Kingdom | 546/201 |
| 1422295 | 1/1976 | United Kingdom | 544/373 |
| 2073738 | 10/1981 | United Kingdom | 544/373 |

OTHER PUBLICATIONS

Derwent Abstract, U.K. 1,410,783.
Derwent Abstract, DOS 23 37 461.
Derwent Abstract, DOS 23 02 717.
Derwent Abstract, EP 5828.

*Primary Examiner*—Donald G. Daus
*Assistant Examiner*—S. A. Gibson
*Attorney, Agent, or Firm*—Gerald D. Sharkin; Robert S. Honor

[57] ABSTRACT

The compounds of formula I,

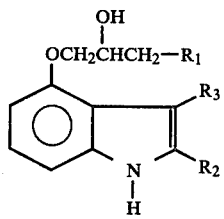

where $R_1$, $R_2$ and $R_3$ have various significances, and physiologically acceptable hydrolyzable derivatives thereof having the hydroxy group in the 2 position of the 3-aminopropoxy side chain in esterified form, are useful as cardiotonic, antiarrhythmic, α- and β-adrenoceptor blocking agents.

11 Claims, No Drawings

2-CYANO-4-(2-HYDROXY-3-SUBSTITUTED-AMINOPROPOXY) INDOLES

The present invention relates to 3-aminopropoxyaryl derivatives, their preparation and pharmaceutical compositions containing them.

In accordance with the invention there are provided compounds of formula I,

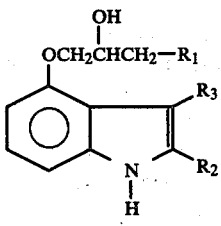
I wherein either
(A) $R_1$ is:
(a) a group —B—CO—$R_h$, wherein
B is a group (i), (ii) or (iii), groups (i), (ii) and (iii) having the following significances:

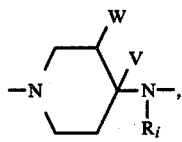
(i)

wherein
V and W are hydrogen or together form an additional bond,
$R_i$ is hydrogen, alkyl of 1 to 4 carbon atoms, phenyl or phenyl monosubstituted or independently disubstituted by alkyl of 1 to 4 carbon atoms, alkoxy of 1 to 4 carbon atoms or halogen of atomic number of from 9 to 35;

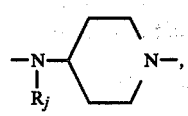
(ii)

wherein $R_j$ is hydrogen or alkyl of 1 to 4 carbon atoms;

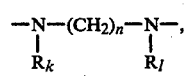
(iii)

wherein
n is 2, 3 or 4,
$R_k$ has the significance indicated above for $R_j$ and
$R_l$ has the significance indicated above for $R_i$, and
$R_h$ is phenylalkyl of 7 to 11 carbon atoms or diphenylalkyl of 13 to 17 carbon atoms, any of the phenyl rings of these two radicals optionally being mono- or independently disubstituted by alkyl of 1 to 4 carbon atoms, alkoxy of 1 to 4 carbon atoms or halogen of atomic number of from 9 to 35;
(b) a group

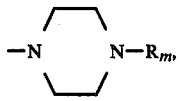

wherein
$R_m$ is —$COR_n$ or —$R_p$, wherein
$R_n$ has the significance indicated above for $R_h$ and
$R_p$ has the significance indicated above for $R_h$ or is phenyl independently disubstituted by alkyl of 1 to 4 carbon atoms, alkoxy of 1 to 4 carbon atoms or halogen of atomic number of from 9 to 35,
$R_2$ is hydroxy and
$R_3$ is hydrogen or
(B) $R_l$ is a group (i'), (ii') or (iii'), groups (i'), (ii') and (iii') having the following significances:

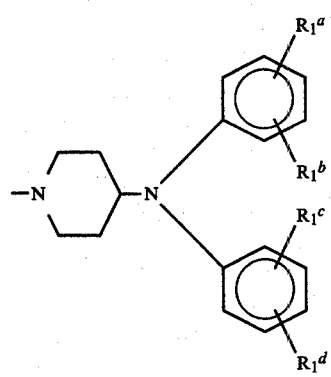
(i')

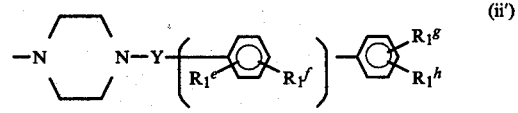
(ii')

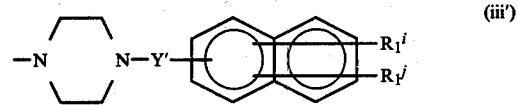
(iii')

wherein
Y and Y' are a bond or methylene, and
$R_{la}$ to $R_{ij}$ are hydrogen, alkyl of 1 to 4 carbon atoms, alkoxy of 1 to 4 carbon atoms or halogen of atomic number of from 9 to 35,
$R_2$ is hydrogen, methyl, hydroxymethyl, carboxyl, alkoxycarbonyl of 2 to 5 carbon atoms, carbamoyl or cyano and
$R_3$ is hydrogen or methyl, or
(c) $R_l$ is a group (i'') or (ii''), groups (i'') and (ii'') having the following significances:

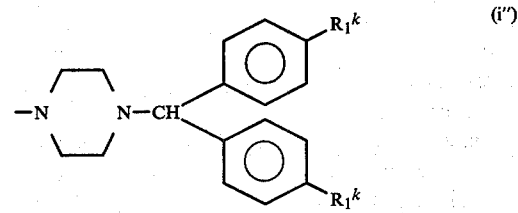
(i'')

-continued

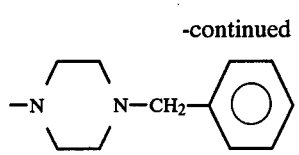 (ii″)

wherein $R_{lk}$ is either methoxy or chloro, $R_2$ is cyano and $R_3$ is hydrogen, and physiologically acceptable hydrolyzable derivatives thereof having the hydroxy group in the 2 position of the 3- aminopropoxy side chain in esterified form, hereinafter referred to as "the compounds of the invention".

It is to be appreciated that for the sake of simplicity the compounds of the invention are defined, e.g., when $R_2$ is hydroxy, with reference to the tautomeric form of formula I. However, the invention extends to all tautomeric forms of the compounds, e.g. when $R_2$ is hydroxy, to the oxindol form.

A physiologically hydrolyzable derivative is a derivative which under physiological conditions is split to the corresponding compound having a hydroxy group in the 2 position of the 3-aminopropoxy side chain.

A group of compounds of the invention is the compounds of formula I, wherein $R_1$, $R_2$, and $R_3$ are as defined under A) and B) above, and physiologically acceptable hydrolyzable derivatives thereof having the hydroxy group in the 2 position of the 3-amino-propoxy side chain in esterified form, and the compounds of formula I, wherein $R_1$, $R_2$ and $R_3$ are as defined under (C) above.

Another group of compounds of the invention is the compounds of formula I, wherein $R_1$, $R_2$ and $R_3$ are as defined under (A) above, and physiologically acceptable hydrolyzable derivatives thereof having the hydroxy group in the 2 position of the 3-amino-propoxy side chain in esterified form.

Another group is the compounds of formula I, wherein $R_1$ is as defined under (B)(i′) above and $R_2$ and $R_3$ are as defined under (B) above, and physiologically acceptable hydrolyzable derivatives thereof having the hydroxy group in the 2 position of the 3-aminopropoxy side chain in esterified form.

Another group is the compounds of formula I, wherein $R_1$ is as defined under (B)(ii′) above and $R_2$ and $R_3$ are as defined under (B) above, and physiologically acceptable hydrolyzable derivatives thereof having the hydroxy group in the 2 position of the 3-aminopropoxy side chain in esterified form.

Another group is the compounds of formula I, wherein $R_1$ is as defined under (B)(iii′) above and $R_2$ and $R_3$ are as defined under (B) above, and physiologically acceptable hydrolyzable derivatives thereof having the hydroxy group in the 2 position of the 3-aminopropoxy side chain in esterified form.

Another group is the compounds of formula I, wherein $R_1$, $R_2$ and $R_3$ are as defined under (C) above.

A group of derivatives in esterified form of the compounds of formula I is e.g. the compounds of formula E,

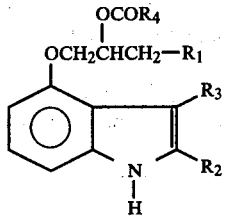 E wherein $R_1$, $R_2$ and $R_3$ are as defined above, and $R_4$ is alkyl of 1 to 12 carbon atoms, cycloalkyl of 3 to 7 carbon atoms, phenyl, phenylalkyl of 7 to 12 carbon atoms, phenyl or phenylalkyl of 7 to 12 carbon atoms monosubstituted in the phenyl ring by alkyl of 1 to 4 carbon atoms, or mono- or independently disubstituted in the phenyl ring by halogen of atomic number of from 9 to 35, or mono-or independently di- or independently tri- substituted in the phenyl ring by alkoxy of 1 to 4 carbon atoms.

Preferred are the compounds wherein the hydroxy group in the 2 position of the 3-aminopropoxy side chain is in unesterified form.

Any monosubstituted phenyl ring appearing in or as a substituent preferably is substituted in the para position. Any disubstituted phenyl ring preferably is substituted in the meta and para positions. Any trisubstituted phenyl ring preferably is substituted in the meta, meta and para positions. any phenyl ring preferably is unsubstituted, mono- or disubstituted. Any polysubstituted phenyl ring preferably is substituted by identical substituents.

Alkyl and/or alkoxy preferably is of 1 or 2 carbon atoms, especially of 1 carbon atom. Halogen preferably is chlorine or bromine, especially chlorine. Phenylalkyl preferably is of 7 to 9 carbon atoms, especially of 7 carbon atoms. Diphenylalkyl preferably is of 13 to 15 carbon atoms, especially of 13 carbon atoms. Alkoxycarbonyl preferably is of 2 or 3 carbon atoms, especially of 2 carbon atoms. When it is of more than 3 carbon atoms, it preferably is branched in the $\alpha$ position, as in isopropoxycarbonyl.

$R_1$ preferably has the significance (A)(b), (B) or (C) defined above. $R_2$ preferably is hydroxy or cyano. $R_3$ preferably is hydrogen. B preferably is a group (i) as defined above. V and W preferably are hydrogen. $R_i$ and/or $R_l$ preferably is hydrogen or alkyl. $R_j$ and/or $R_k$ preferably is hydrogen. n preferably is 2. $R_h$ and/or $R_n$ preferably is diphenylalkyl. $R_m$ preferably is $R_p$. $R_p$ preferably is unsubstituted or substituted phenylalkyl or diphenylalkyl, especially unsubstituted or substituted diphenylalkyl. When $R_1$ is a group (i′), (ii′), or (iii′), it preferably is a group (i′) or (ii′). Y and/or Y′ preferably is methylene. $R_{1a}$ to $R_{1j}$ preferably are hydrogen, alkoxy or halogen. When $R_1$ is a group (i″) or (ii″), it preferably is a group (ii″). When $R_1$ is a group (ii′), the phenyl ring carrying $R_{1g}$ and $R_{1h}$ is preferably is bound at the 4 position of the phenyl ring carrying $R_{1e}$ and $R_{1f}$. When $R_1$ is a group (iii′), the naphthalene ring preferably is bound at the 1 position with Y′.

a preferred group of compounds of the invention is the compounds of formula Is,

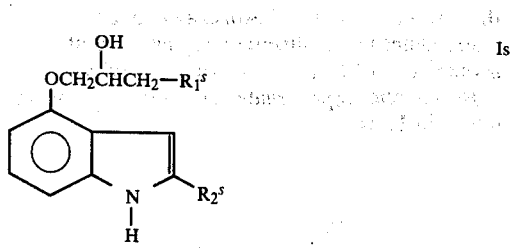

wherein either (A') $R_{1s}$ is a group

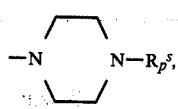

wherein p $R_{ps}$ is diphenylalkyl of 13 to 17 carbon atoms, any of the phenyl rings of this radical optionally being mono- or independently disubstituted by alkoxy of 1 to 4 carbon atoms or halogen or atomic number of from 9 to 35 and $R_{2s}$ is hydroxy, or (B') $R_{1s}$ is a group

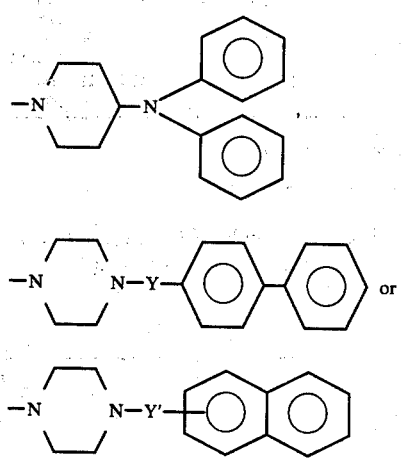

wherein Y and Y' are as defined above, and $R_{2s}$ is cyano, or (C') $R_{1s}$ is a group (i'') or (ii''), as defined above, and $R_{2s}$ is cyano.

In accordance with the invention, a compound of the invention may be obtained by a process which includes the step of appropriately 3-amino-2-oxypropylating a corresponding compound of formula IV,

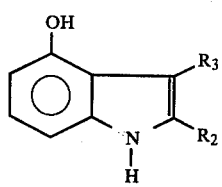

wherein $R_2$ and $R_3$ are as defined above, or a precursor form thereof.

The process step of the invention may be effected in conventional manner for the production of analogous 3-amino-2-oxy-propoxyaryl compounds.

The choice of the most appropriate variant should, of course, take into account the reactivities of the substituents present.

Preferably a compound of formula IV is used, rather than a precursor form thereof.

A precursor form of a compound of formula IV is a compound capable of being converted into a compound of formula IV, e.g. by appropriate acylation, or by deprotection. Thus, when $R_2$ is alkoxycarbonyl, a precursor form is e.g. a corresponding compound wherein $R_2$ is carboxyl.

Thus, the process step of the invention may be effected in more than one stage. For example, a compound of formula IV in protected form may be used, or a 3-amino-2-oxypropyl moiety in protected form may be introduced, and subsequently, after the 3-amino-2-oxypropylation has been effected, any protecting group present may be split off.

Benzyl, methyl or tetrahydropyranyl, preferably benzyl, are examples of a protecting group.

In one form of the process according to the invention, the 3-amino-2-oxypropylation is effected in two main stages.

In a first stage, a group $-CH_2-R_x$, wherein $R_x$ is a group capable of reacting with a primary or secondary amine to give a 2-amino-1-hydroxyethyl group, is introduced by O-alkylation into a compound of formula IV to give a corresponding compound of formula II,

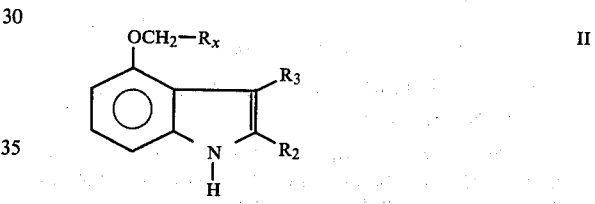

wherein $R_x$, $R_2$ and $R_3$ are as defined above.

In a second stage, a compound of formula II is reacted with a corresponding compound of formula III, $$H-R_1 \qquad III$$

wherein $R_1$ is as defined above, and where required, the 2 position of the 3-amino-propoxy side chain in a resultant compound of formula I is appropriately esterified.

The 0-alkylation stage may be effected in a manner known for the production of analogous ethers. A compound of formula IV preferably is reacted in anionic form.

The amination stage may be effected in conventional manner for the production of analogous 3-amino-2-hydroxypropoxyaryl compounds. For example, $R_x$ may be a group of formula

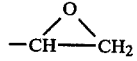

or a derivative of this group, e.g. a group of formula —CH(OH)—CH$_2$L, wherein L is chlorine, bromine or a group $R_y$—SO$_2$13 O—, where $R_y$ is phenyl, tolyl or lower alkyl. L is especially chlorine. The reaction is preferably effected in ethanol or in an appropriate ether such as dioxane. Optionally an excess of the amine may be used as solvent. Alternatively, the reaction may be effected in a fusion melt. Suitable reaction temperatures may be from about 20 to about 200° C., conveniently the reflux temperature of the reaction mixture when a solvent is present.

The optional esterification of the 2 hydroxy group in the 3-aminopropoxy side chain may be effected in manner known for the production of analogous esters of 3-amino-2- hydroxypropoxyaryl compounds, is necessary using selective reactions when other reactive groups, e.g. amino, are present.

The compounds of the invention may exist in free form, i.e. normally as a base, or in salt form, e.g. acid addition salt from. Free forms of the compounds of the invention may be converted into salt forms and vice versa, in conventional manner. Suitable acids for acid addition salt formation include hydrochloric, malonic and fumaric acid.

In the compounds of the invention, the carbon atom in e.g. the 2 position of the 3-aminopropoxy side chain is asymmetrically substituted. The compounds may thus exist in the racemic form or in individual optical isomer form. The preferred optical isomer has the S-configuration at this asymmetrically substituted carbon atom of the 3-aminopropoxy side chain. Individual optical isomer forms may be obtained in conventional manner, for example by using optically active starting materials or by fractional crystallisation of racemate salts using optically active acids.

Inosfar as the preparation of any particular starting material is not particularly described, this may be effected in conventional manner.

In the following Examples all temperatures are in degrees Centigrade and are uncorrected.

Example 1: 4-[3-[4-(diphenylmethyl)-1-piperazinyl]-2-hydroxypropoxyly]-1H-indol-2(3H)-on 2 g of 4- (2,3-epoxypropoxy)-1H-indol-2(3H)-on and 2.5 g of 1-(diphenylmethyl)piperazine dissolved in 50 ml dioxan are heated under refluxing for 17 hours. The solvent is then evaporated to dryness under vacuum, the resultant yellow oil is dissolved in ethanol and ether is added until crystallization begins. The title compound is obtained (M.P. 162-164° -from ethyl acetate).

From the appropriate compound of formula II, wherein $R_x$ is

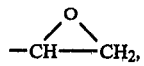

the following compounds of formula I may be obtained by reaction with the appropriate compounds of formula III in analogous manner to Example 1:

| Example No. | $R_1$ | $R_2$ | $R_3$ | M.P. |
|---|---|---|---|---|
| 2 | 4-(2,2-diphenylethyl)-1-piperazinyl | OH | H | b 113–116° |
| 3 | 4-(4,4'-dimethoxydiphenylmethyl)-1-piperazinyl | OH | H | b 113–114.5° |
| 4 | 4-(4,4'-dichlorodiphenylmethyl)-1-piperazinyl | OH | H | b 116–119° |
| 5 | 4-diphenylaminopiperidin-1-yl | CN | H | hmo 124–126° |
| 6 | 4-(1,1'-diphenyl-4-ylmethyl)-piperazin-1-yl | CN | H | b 164–166° |
| 7 | 4-(naphthalin-1-ylmethyl)piperazin-1-yl | CN | H | zml 167–170° |
| 8 | 4-(4,4'-dimethoxydiphenylmethyl)-1-piperazinyl | CN | H | zml 114–116° |
| 9 | 4-(4,4'-dichlorodiphenylmethyl)-1-piperazinyl | CN | H | ml 140–143° |
| 10 | 4-benzylpiperazin-1-yl | CN | H | zml 203–204° | b = in free base form
hmo = hydrogen malonate salt form
ml = in maleate salt form
zml = bis [base ]hydrogen maleate salt form The following compounds of formula I may also be obtained in a manner analogous to Example 1:

| Ex. | $R_1$ | $R_2$ | $R_3$ |
|---|---|---|---|
| A | [structure with -N-piperidinyl-NHCO(CH$_2$)$_3$-phenyl-CH$_2$CH$_2$CH$_3$] | OH | H |
| B | [structure with -NH-piperidinyl-N-COCH$_2$CH(CH$_2$CH$_3$)CH-phenyl(Cl)-phenyl(OCH$_3$)] | OH | H |
| C | [structure with -N-piperidinyl-N-COCH$_2$-phenyl(Br)-phenyl(Cl,OCH$_3$,OCH(CH$_3$)$_2$)] | OH | H |

-continued

| Ex. | R₁ | R₂ | R₃ |
|---|---|---|---|
| D | —N(piperidin-4-yl)—N(CH₂CH₂CH₃)COCH₂CH₂CH(CH₃)₂—C₆H₄—OCH₃ | OH | H |
| E | —N(piperidin-4-yl with C(CH₃)₃)—N—CO(CH₂)₂CH(C₆H₅)—C₆H₄ (biphenyl) | OH | H |
| F | —NH(CH₂)₂N(CH₂CH₃)COCH(CH₃)CH₂—C₆H₃(OCH₃)(CH₃) | OH | H |
| G | —N(CH₂CH₃)(CH₂)₄NHCO(CH₂)₄CH(—C₆H₄Br)(—C₆H₃(CH₃)(OCH₃)) | OH | H |
| H | —N[(CH₂)₃—N(CO(CH₂)₂—C₆H₄—F)(—C₆H₄—CH₂CH₃)]—CH(CH₃)₂ | OH | H |
| I | —N(piperazin-1-yl)—N—COCH₂—C₆H₃(OCH₂CH₃)(Cl) | OH | H |
| J | —N(piperazin-1-yl)—N—COCH(—C₆H₄—OCH₃)(—C₆H₃(Br)(F)) | OH | H |
| K | —N(piperazin-1-yl)—N—C₆H₃(F)(CH₂CH(CH₃)₂) | OH | H |

-continued

| Ex. | R₁ | R₂ | R₃ |
|---|---|---|---|
| L | -N(piperazine)N-(2-OCH₂CH₃, 4-Cl-phenyl) | OH | H |
| M | -N(piperazine)N-CH(CH₂CH₃)CH₂-phenyl | OH | H |
| N | -N(piperazine)N-CH(CH₂CH₃)CH(phenyl)(phenyl) | OH | H |
| O | -N(piperidine-4-yl)-N(phenyl)(3-CH₂CH₃-phenyl) | H | H |
| P | -N(piperidine-4-yl)-N(phenyl)(3-OCH(CH₃)₂-phenyl) | COOH | CH₃ |
| Q | -N(piperazine)N-CH₂-(2-OCH₃, 3-CH₃, 5-(3-Cl-phenyl)-phenyl) | CH₃ | CH₃ |
| R | -N(piperazine)N-(4-F, 3-phenyl-phenyl) | COO(CH₂)₃CH₃ | H |
| S | -N(piperazine)N-CH₂-(naphthyl, OC(CH₃)₃, Br substituted) | CH₂OH | CH₃ |

-continued

| Ex. | R₁ | R₂ | R₃ |
|---|---|---|---|
| T | 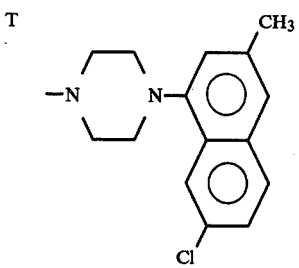 | CONH₂ | CH₃ |

The following derivatives, esters of the compounds of formula I (which are compounds of formula E) may be obtained by appropriately esterifying the 2 position of the 3-amino-propoxy side chain in the corresponding compound of formula I (the other substituents are as for the corresponding compound of formula I):

| Ex. No. | Corresponding compound of formula I (Ex. No.) | R₄ (formula E) |
|---|---|---|
| 1-E | 1 | n-nonyl |
| 2-E | 2 | 3-ethylbenzyl |

The compounds of the invention are useful because they exhibit pharmacological activity in animals.

The compounds possess cariotonic activity, as indicated by standard tests. For example, in the normotonic Numal anaesthetized dog, an increase in the contractile force of the left ventricle is observed upon intravenous administration of from about 0.2 to about 2 mg/kg.

Thus, the increases in contractile force measured for the compounds of Examples 1, 2, 3 and 6 are, respectively, 41, 25, 38 and 11% at the dose of 2 mg/kg i.v.

For the standard compound digoxine at a dose of 0.08 mg/kg i.v., the increase measured is 45%. Amrinone at a dose of 2 mg/kg i.v. increase contractile force by 83%.

The test method is as follows:

Dogs of either sex weighing from 10 to 15 kg are used. Numal in a dose of 65 mg/kg i.v. is used as an anaesthetic. The animal is attached in supine position on the operation table. After the usual preparations have been effected, a heparinized catheter is introduced along the Arteria carotis dextra into the left ventricle under radiologic control and the transmission of the pressure is registered with a donor membrane (Gould Statham P 23 Gb). The increase in pressure as a function of time is computed and registered with an HSE-physiodifferentiator. The pressure increase in the left ventricle is a measure of the contractile force of the heart. The magnitude of the pressure differential is indicated in mm Hg/$_{sec}$. A suitable body temperature (about 36 to 37° C.) is maintained constant. After a control period of about 40 minutes the test substance is injected into the Vena femoralis and its effect on the registered or computed parameters observed.

The compounds are therefore useful as cardiotonic agents, e.g. for the treatment of heart insufficiency.

Preferred in this indication are the compounds of Examples 1, 2, 3 and 6, especially of Examples 1 and 3.

For the above-mentioned cardiotonic use the dosage will, of course, vary depending on the compound employed, mode of administration and treatment desired. However, in general, satisfactory results are obtained when administered at a daily dosage of from about 0.1 mg to about 10 mg per kg animal body weight, conveniently given in divided doses 2 to 4 times a day or in sustained release form. For the larger mammals, the total daily dosage is in the range of from about 1 mg to about 500 mg, and dosage forms suitable for oral administration comprise from about 0.25 mg to about 250 mg of the compounds admixed with a solid or liquid pharmaceutical carrier or diluent. An example of a daily dosage is from 10 mg to 500 mg.

The compounds also exhibit antiarrhythmic activity, as indicated in standard tests. For example, they prolong the functional refractory period in the left guinea pig atrium at a concentration of from $10^{-6}$ to $10^{-4}$ M in accordance with the methodogical principles of N. Reuter and E. Heeg [Arch.Pharmakol. 268 (1971) 323-333].

The compounds are therefore useful as antiarrhythmic agents, e.g. for the treatment of heart rhythm disorders.

The compounds also exhibit α-adrenoceptor blocking activity, as indicated by standard tests. For example, the inhibition of α-adrenoceptors may be observed in isolated spiral strips of the Vena femoralis of dogs (E. Müller-Schweinitzer and E. Stürmer, Br. J. Pharmacol. [1974], 51, 441-446), at a bath concentration of from about $10^{-7}$ M to about $10^{-5}$ M.

The compounds are therefore useful as α-adrenoceptor blocking agents, e.g. for the prophylaxis and treatment of disorders related to a paralysis of intestine motility, such as paralytic ileus.

The compounds also possess β-adrenoceptor blocking activity, as indicated by standard tests. For example, in isolated, spontaneously-beating guinea pig atria (method of A. Bertholet et al., Postgrad. Med. J. [1981] 57 [Suppl. 1] 9-17) inhibition of the positive chronotropic effect of isoprenaline is observed at a bath concentration of about $10^{-9}$ M to about $10^{-6}$ M.

The compounds are therefore useful as β-adrenoceptor blocking agents, e.g. for the prophylaxis and treatment of Angina pectoris, hypertension and myocardial infarction.

For the above-mentioned antiarrhythmic and α- and β-adrenoceptor blocking uses the dosage will, of course, vary depending on the compound employed, mode of administration and treatment desired. However, in general, satisfactory results are obtained when administered at a daily dosage of from about 0.001 mg to about 100 mg per kg animal body weight, conveniently given in divided doses 2 to 4 times a day or in sustained release form. For the larger mammals, the total daily dosage is in the range of from about 0.1 mg to about 1000 mg, and dosage forms suitable for oral administration comprise from about 0.025 mg to about 500 mg of the compounds admixed with a solid or liquid pharmaceutical carrier or diluent. Examples of daily doses are from 0.1 mg to 100 mg.

In general, the 2(S) optical isomers of the compounds are more active than the 2(R) optical isomers as β-adrenoceptor-blocking agents.

It will be appreciated that it may be necessary to convert a compound having the hydroxy group in the 2 position of the 3-aminopropoxy side chain in esterified form to the corresponding unesterified compound prior to carrying out the in vitro tests indicated above for showing activity.

The cardiotonic use is the preferred use of the compounds.

The compounds may be administered in pharmaceutically acceptable salt form. Such salt forms exhibit the same order of activity as the free forms and are readily prepared in conventional manner. The present invention also provides a pharmaceutical composition comprising a compound of the invention in free form or in pharmaceutically acceptable salt form, in association with a pharmaceutical carrier or diluent. Such compositions may be in the form of, for example, a solution or a tablet.

The compounds of formula I may be administered in similar manner to known standards for use in these utilities, for example for the cardiotonic use, digoxine or amrinone. The suitable daily dosage for a particular compound will depend on a number of factors such as its relative potency of activity.

In a first group of compounds B is a group (i).
In a 2nd group of compounds B is a group (ii).
In a 3rd group of compounds B is a group (iii).
In a 4th group of compounds $R_1$ is a group

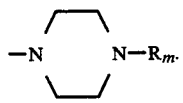

In a 5th group of compounds $R_m$ is -$COR_n$.
In a 6th group of compounds $R_m$ is -$R_p$.
In a 7th group of compounds $R_h$ is unsubstituted or substituted phenylalkyl.
In a 8th group of compounds $R_h$ is unsubstituted or substituted diphenylalkyl.
In a 9th group of compounds $R_n$ is unsubstituted or substituted phenylalkyl.
In a 10th group of compounds $R_n$ is unsubstituted or substituted diphenylalkyl.
In a 11th group of compounds $R_p$ is unsubstituted or substituted phenylalkyl.
In a 12th group of compounds $R_p$ is unsubstituted or substituted diphenylalkyl.
In a 13th group of compounds $R_p$ is disubstituted phenyl.
In a 14th group of compounds $R_1$ is a group (i').
In a 15th group of compounds $R_1$ is a group (ii').
In a 16th group of compounds $R_1$ is a group (iii').
In a 17th group of compounds $R_2$ is cyano and $R_1$ is a group (i'), (ii') or (iii').
In a 18th group of compounds $R_3$ is hydrogen.
In a 19th group of compounds $R_3$ is methyl.
In a 20th group of compounds $R_1$ is a group (i'').
In a 21th group of compounds $R_1$ is a group (ii'').

I claim:
1. A compound of formula I

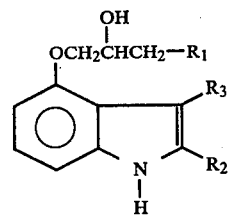

wherein either
(A) $R_1$ is:
(a) a group —B—CO—$R_h$, wherein B is a group (i), (ii) or (iii), groups (i), (ii) and (iii) having the following significances:

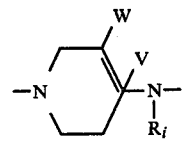

wherein
V and W are hydrogen or together form an additional bond,
$R_i$ is hydrogen, alkyl of 1 to 4 carbon atoms, phenyl or phenyl monosubstituted or independently disubstituted by alkyl of 1 to 4 carbon atoms, alkoxy of 1 to 4 carbon atoms or halogen of atomic number of from 9 to 35;

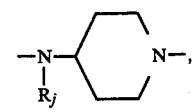

wherein $R_j$ is hydrogen or alkyl of 1 to 4 carbon atoms;

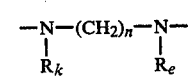

wherein
n is 2, 3 or 4,
$R_k$ has the significance indicated above for $R_j$ and
$R_e$ has the significance indicated above for $R_i$, and
$R_h$ is phenylalkyl of 7 to 11 carbon atoms or diphenylalkyl of 13 to 17 carbon atoms, any of the phenyl rings of these two radicals optionally being mono or independently disubstituted by alkyl of 1 to 4 carbon atoms, alkoxy of 1 to 4 carbon atoms or halogen of atomic number of from 9 to 35;
(b) a group

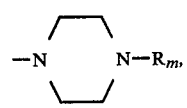

wherein
$R_m$ is —$COR_n$ or —$R_p$, wherein
$R_n$ has the significance indicated above for $R_h$ and $R_p$ has the significance indicated above for $R_h$ or is phenyl independently disubstituted by alkyl of 1 to 4 carbon atoms, alkoxy of 1 to 4 carbon atoms or halogen of atomic number of from 9 to 35, $R_2$ is hydroxy and $R_3$ is hydrogen or (B) $R_1$ is a group (i'), (ii') or (iii'), groups (i'), (ii') and (iii') having the following significances:

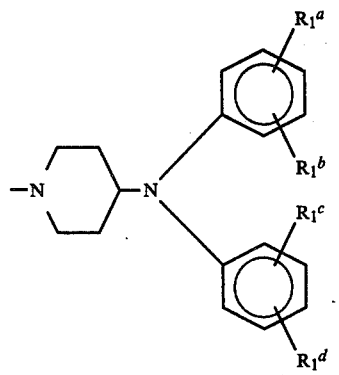

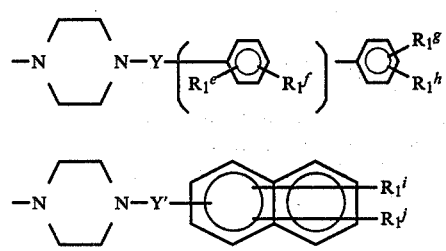

wherein

Y and Y' are a bond or methylene, and $R_1{}^a$ to $R_1{}^j$ are hydrogen, alkyl of 1 to 4 carbon atoms, alkoxy of 1 to 4 carbon atoms or halogen of atomic number of from 9 to 35, $R_2$ is hydrogen, methyl, hydroxymethyl, carboxyl, alkoxycarbonyl of 2 to 5 carbon atoms, carbamoyl or cyano and $R_3$ is hydrogen or methyl, and physiologically acceptable hydrolyzable derivatives thereof having the hydroxy group in the 2 position of the 3-aminopropoxy side chain in esterified form, or a pharmaceutically acceptable salt form thereof.

2. The compound of claim 1 of formula I, wherein $R_1$ is 4-(diphenylmethyl)-1-piperazinyl, $R_2$ is hydroxy and $R_3$ is hydrogen, or a pharmaceutically acceptable salt form thereof.

3. A pharmaceutical composition comprising a compound of claim 1 in association with a pharmaceutical carrier or diluent.

4. A method of treating heart insufficiency, which comprises administering to an animal in need of such treatment a therapeutically effective amount of a compound of claim 1.

5. A compound of formula I of claim 1 wherein either (A) $R_1$ is:

(a) a group —B—CO—$R_h$, wherein B is a group (i), (ii) or (iii), groups (i), (ii) and (iii) having the following significances:

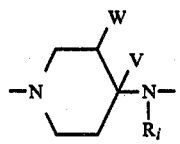

wherein

V and W are hydrogen or together form an additional bond, $R_i$ is hydrogen, alkyl of 1 to 4 carbon atoms, phenyl or phenyl monosubstituted or independently disubstituted by alkyl of 1 to 4 carbon atoms, alkoxy of 1 to 4 carbon atoms or halogen of atomic number of from 9 to 35;

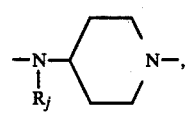

wherein $R_j$ is hydrogen or alkyl of 1 to 4 carbon atoms;

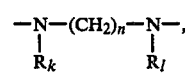

wherein n is 2, 3 or 4, $R_k$ has the significance indicated above for $R_j$ and $R_e$ has the significance indicated above for $R_i$, and $R_h$ is phenylalkyl of 7 to 11 carbon atoms or diphenylalkyl of 13 to 17 carbon atoms, any of the phenyl rings of these two radicals optionally being mono- or independently disubstituted by alkyl of 1 to 4 carbon atoms, alkoxy of 1 to 4 carbon atoms or halogen of atomic number of from 9 to 35;

(b) a group

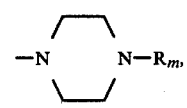

wherein $R_m$ is —$COR_n$ or —$R_p$, wherein $R_n$ has the significance indicated above for $R_h$ and $R_p$ has the significance indicated above for $R_h$ or is phenyl independently disubstituted by alkyl of 1 to 4 carbon atoms, alkoxy of 1 to 4 carbon carbon atoms or halogen of atomic number of from 9 to 35, $R_2$ is hydroxy and $R_3$ is hydrogen or (B) $R_1$ is a group (i'), (ii') or (iii'), groups (i'), (ii'), and (iii') having the following significances:

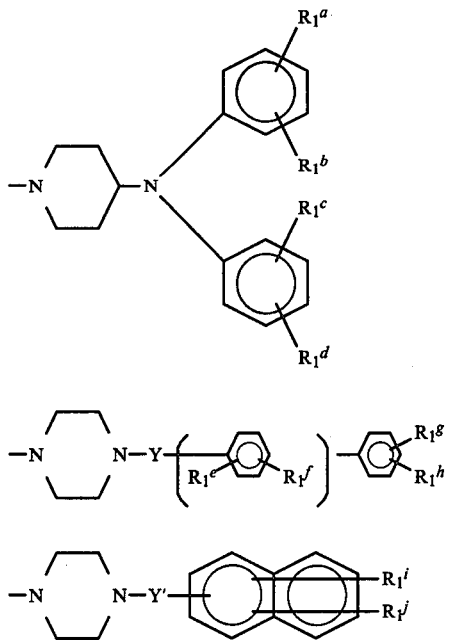

(i')

(ii')

(iii')

wherein
Y and Y' are a bond or methylene, and
$R_1{}^a$ to $R_1{}^j$ are hydrogen, alkyl of 1 to 4 carbon atoms, alkoxy of 1 to 4 carbon atoms or halogen of atomic number of from 9 to 35, $R_2$ is hydrogen, methyl, hydroxymethyl, carboxyl, alkoxycarbonyl of 2 to 5 carbon atoms, carbamoyl or cyano and $R_3$ is hydrogen or methyl, and physiologically acceptable hydrolyzable derivatives thereof having the hydroxy group in the 2 position of the 3-aminopropoxy side chain in esterified form, or a pharmaceutically acceptable salt form thereof.

6. A compound of formula I of claim 1 wherein either
(A) $R_1$ is:
(a) a group —B—CO—$R_h$, wherein B in a group (i), (ii) or (iii), groups (i), (ii) and (iii) having the following significances:

(i)

wherein
V and W are hydrogen or together form an additional bond,
$R_i$ is hydrogen, alkyl of 1 to 4 carbon atoms, phenyl or phenyl monosubstituted or independently disubstituted by alkyl of 1 to 4 carbon atoms, alkoxy of 1 to 4 carbon atoms or halogen of atomic number of from 9 to 35;

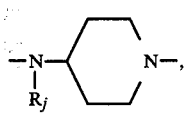

(ii)

wherein $R_j$ is hydrogen or alkyl of 1 to 4 carbon atoms;

$$-\underset{R_k}{N}-(CH_2)_n-\underset{R_l}{N}-,$$ (iii)

wherein
n is 2, 3 or 4,
$R_k$ has the significance indicated above for $R_j$ and
$R_e$ has the significance indicated above for $R_i$, and
$R_h$ is phenylalkyl of 7 to 11 carbon atoms or diphenylalkyl of 13 to 17 carbon atoms, any of the phenyl rings of these two radicals optionally being mono- or independently disubstituted by alkyl of 1 to 4 carbon atoms, alkoxy of 1 to 4 carbon atoms or halogen of atomic number of from 9 to 35;

(b) a group $$-N\diagdown\underset{\diagup}{\phantom{X}}N-R_m,$$

wherein
$R_m$ is —CO$R_n$ or —$R_p$, wherein
$R_n$ has the significance indicated above for $R_h$ and
$R_p$ has the significance indicated above for $R_h$ or is phenyl independently disubstituted by alkyl of 1 to 4 carbon atoms, alkoxy of 1 to 4 carbon carbon atoms or halogen of atomic number of from 9 to 35,
$R_2$ is hydroxy and
$R_3$ is hydrogen or
(B) $R_1$ is a group (i'), (ii') or (iii'), groups (i'), (ii'), and (iii') having the following significances:

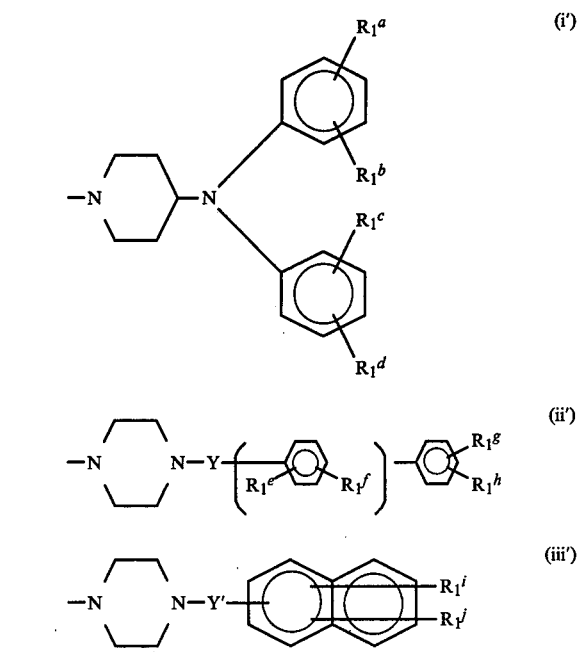

wherein
Y and Y' are a bond or methylene, and
$R_1{}^a$ to $R_1{}^j$ are hydrogen, alkyl of 1 to 4 carbon atoms, alkoxy of 1 to 4 carbon atoms or halogen of atomic number of from 9 to 35, $R_2$ is hydrogen, methyl, hydroxymethyl, carboxyl, alkoxycarbonyl of 2 to 5 carbon atoms, carbamoyl or cyano and $R_3$ is hydrogen or methyl, and physiologically acceptable hydrolyzable derivatives thereof having the hydroxy group in the 2 position of the 3-aminopropoxy side chain in esterified form, or a pharmaceutically acceptable salt form thereof, and or a pharmaceutically acceptable salt form thereof.

7. A compound of formula is of claim 1

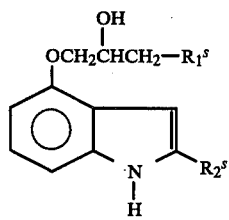

wherein either (A') $R_1{}^s$ is a group

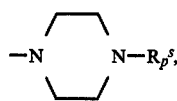

wherein $R_1{}^s$ is diphenylalkyl of 13 to 17 carbon atoms, any of the phenyl rings of this radical optionally being mono- or independently disubstituted by alkoxy of 1 to 4 carbon atoms or halogen of atomic number of from 9 to 35 and $R_2{}^s$ is hydroxy, or (B') $R_1{}^s$ is a group

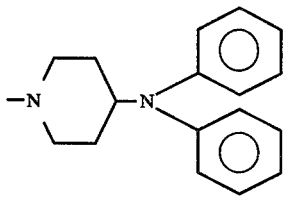

Is

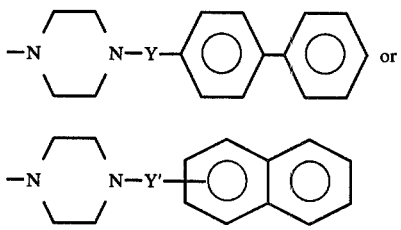

wherein Y and Y' are as defined above, and $R_2{}^s$ is cyano, or a pharmaceutically acceptable salt form thereof.

8. A compound of claim 1 where Y and Y' are methylene.

9. A compound of claim 7 where Y and Y' are methylene.

10. A compound of claim 8 where Y and Y' are methylene.

11. A compound of claim 9 where Y and Y' are methylene.

* * * * *